(12) United States Patent
Tsuji

(10) Patent No.: US 8,013,309 B2
(45) Date of Patent: Sep. 6, 2011

(54) MICROWAVE SENSOR CAPABLE OF PREVENTING FALSE ALARMS DUE TO A BUSH OR TREE OR THE LIKE SWAYING IN THE WIND

(75) Inventor: Masatoshi Tsuji, Otsu (JP)

(73) Assignee: Optex Co., Ltd., Shiga (JP)

( * ) Notice: Subject to any disclaimer, the term of this patent is extended or adjusted under 35 U.S.C. 154(b) by 882 days.

(21) Appl. No.: 11/919,055

(22) PCT Filed: Apr. 20, 2006

(86) PCT No.: PCT/JP2006/308320
§ 371 (c)(1),
(2), (4) Date: Oct. 23, 2007

(87) PCT Pub. No.: WO2006/118041
PCT Pub. Date: Nov. 9, 2006

(65) Prior Publication Data
US 2009/0294670 A1 Dec. 3, 2009

(30) Foreign Application Priority Data
Apr. 26, 2005 (JP) .................................. 2005-128428

(51) Int. Cl.
*G01J 1/42* (2006.01)
*G01S 13/00* (2006.01)
(52) U.S. Cl. ............... 250/393; 250/DIG. 1; 250/336.1; 342/28
(58) Field of Classification Search ......................... None
See application file for complete search history.

(56) References Cited

U.S. PATENT DOCUMENTS

| 6,842,113 B2 * | 1/2005 | Tsuji | 340/554 |
| 7,034,675 B2 * | 4/2006 | DiPoala et al. | 340/522 |
| 2004/0222887 A1 * | 11/2004 | Tsuji | 340/552 |

FOREIGN PATENT DOCUMENTS

JP 5-20558 1/1993

(Continued)

OTHER PUBLICATIONS

International Search Report mailed Jul. 11, 2006 for International Application No. PCT/JP2006/308320 of which the present application is the U.S. National Stage.

(Continued)

*Primary Examiner* — David Porta
*Assistant Examiner* — Carolyn Igyarto
(74) *Attorney, Agent, or Firm* — Wenderoth, Lind & Ponack, L.L.P.

(57) ABSTRACT

A movement distance measuring device that measures, as a movement distance, an amount of change per unit of time in a distance to a detected detection target object, an alarm signal output control device that performs control such that an alarm signal is outputted when the measured movement distance is a predetermined determination threshold value or more, and a determination threshold value varying device that varies the determination threshold value to a larger value when a state in which the movement distance is not less than the determination threshold value continues for not less than a first predetermined period and when a state in which the movement distance is less than the determination threshold value and a difference between the determination threshold value and the movement distance is not greater than a predetermined value continues for not less than a second predetermined period.

10 Claims, 8 Drawing Sheets

FOREIGN PATENT DOCUMENTS

| | | |
|---|---|---|
| JP | 07-037176 | 2/1995 |
| JP | 9-293178 | 11/1997 |
| JP | 11-39574 | 2/1999 |
| JP | 2000-221273 | 8/2000 |
| JP | 2000-348265 | 12/2000 |
| JP | 2001-106029 | 4/2001 |
| JP | 2002-344953 | 11/2002 |
| JP | 2003-207462 | 7/2003 |

OTHER PUBLICATIONS

International Preliminary Report on Patentability mailed Nov. 8, 2007 for International Application No. PCT/JP2006/308320.

Written Opinion of the International Searching Authority mailed Nov. 8, 2007 for International Application No. PCT/JP2006/308320.

* cited by examiner (a)

(b)

(a)

(b)

movement distance determination threshold value
(bush/tree countermeasure level X)

status counter (SC)

status counter (SC) addition/subtraction calculations

| measured movement distance | movement distance determination threshold value (bush/tree countermeasure level) | | |
|---|---|---|---|
| | weak | medium | strong |
| 0.8m | +40 | +30 | +20 |
| 0.6m | +30 | +20 | +10 |
| 0.4m | +20 | +10 | ±0 |
| 0m | +10 | ±0 | ±0 |
| non-detection | −1 | −1 | −1 | movement distance determination threshold value (bush/tree countermeasure level X)

status counter (SC) addition/subtraction calculations

| measured movement distance | movement distance determination threshold value (bush/tree countermeasure level) | | |
|---|---|---|---|
| | none | weak | strong |
| 0.8m | +10 | +10 | +10 |
| 0.6m | +10 | +10 | +10 |
| 0.4m | +10 | +10 | ±0 |
| 0m | +10 | ±0 | −1 |
| non-detection | −1 | −1 | −1 |

MICROWAVE SENSOR CAPABLE OF PREVENTING FALSE ALARMS DUE TO A BUSH OR TREE OR THE LIKE SWAYING IN THE WIND

BACKGROUND OF THE INVENTION

I. Technical Field

The present invention relates to microwave sensors that detect intruders and the like using microwaves, and particularly relates to microwave sensors that more accurately detect only intended detection targets and avoid, as much as possible, occurrences of false alarms to improve reliability.

II. Description of Related Art

Conventionally, microwave sensors having microwaves that are transmitted toward a detection area, and when a human body (intruder) is present in the detection area, reflected waves (microwaves modulated by the Doppler Effect) from the human body are received to detect the human body are known as one type of security device (for example, see JP H07-37176A).

Further still, one type of microwave sensor that has been proposed involves measuring a distance to a detection target object, such as a human body present in the detection area, by using a plurality of microwaves of different frequencies. This type of sensor is configured so that, for example, two types of microwaves of different frequencies are transmitted toward the detection area and a phase difference in two IF signals is detected based on the respective reflected waves. The phase difference correlates to the distance to the detection target object, such that there is a tendency for greater phase differences to occur for greater distances to the detection target object. That is, it is possible to measure the distance to the detection target object by obtaining the phase difference. Furthermore, it is possible to determine whether or not the detection target object in the detection area is moving by recognizing change in the phase difference over time. In this way it becomes possible to identify only detection target objects that are moving in the detection area.

For example, when IF output signals based on reflected waves of two types of microwaves of different frequencies are sine waves IFout1 and IFout2 (having a phase difference corresponding to the distance to the detection target object) as shown in FIG. 2(a) and FIG. 2(b), rectangular waves W1 and W2 obtained by performing waveform shaping on these IF signal outputs are as shown in FIG. 3(a) and FIG. 3(b). Then, by detecting a phase difference $\Delta\phi$ of the rectangular waves W1 and W2 (calculated from a time difference $\Delta t$ of a rising portion of the rectangular waves in the diagram), it is possible to measure a distance to the detection target object. Furthermore, by recognizing change over time in the phase difference of the rectangular waves W1 and W2, it is possible to recognize movement of the detection target object in the detection area (whether it is moving toward or away from the sensor).

In this regard, problems, such as the following, arise when using this type of sensor as a security sensor and recognizing change over time in the phase difference to recognize only the detection target object moving in the detection area.

That is, when this type of sensor is installed outside, it is possible that a phase difference will be produced in the rectangular waves W1 and W2 by a tree or a bush or the like swaying in the wind, thus causing a false alarm by inadvertently detecting the tree or bush as a detection target object. Similarly, when this type of sensor is installed inside, it is possible that a phase difference will be produced in the rectangular waves W1 and W2 also by a rotational operation of a ventilation fan, blinds or curtains or the like swaying due to the wind, or even by vibration or the like of the microwave sensor itself, and in these cases too a false alarm is produced by inadvertently detecting an object other than a human body as a detection target object.

Accordingly, the inventor of the present invention already has proposed techniques in which false alarms are avoided by accurately distinguishing between detection target objects such as human bodies and objects that are not targeted for detection, such as trees and fans and the like (see JP 2003-207462A).

These proposals involve measuring an amount of change per unit of time in a relative distance to an object (a movement distance of an object) that is present in a detection area based on reflected waves, and determining that the object is a detection target object only when the movement distance is a predetermined determination threshold or greater. That is, in contrast to the slight movement distance of a bush or tree swaying in the wind or a rotating fan, the movement distance is large for a detection target object such as a human body, and therefore by recognizing this difference a determination can be performed precisely as to whether or not the object is a detection target object. It should be noted that in the following description, these false alarm countermeasures are referred to as "bush/tree countermeasures" and the aforementioned determination threshold is referred to as "bush/tree countermeasure level".

However, it is difficult to set the bush/tree countermeasure level appropriately. That is, when the bush/tree countermeasure level is set undesirably low (a state in which an object is detected even when the movement distance of the detected object is small), under a condition in which a bush or tree sways in the wind by a range of several tens of centimeters, the bush or tree will be inadvertently recognized as a detection target object and a false alarm will occur. In particular, this type of microwave sensor is often used in combination with a passive-type infrared sensor (PIR sensor) in which an intruder is detected from a difference between the human body and the ambient temperature after infrared rays are received from the human body in the detection area (a combined sensor), and in a case where the bush/tree countermeasure level is set low, there is a possibility that the microwave sensor will go into a state of continuously issuing alarms. When this happens, there is essentially no difference from a sensor device configured as a standalone PIR sensor, resulting in reductions in reliability as a combined sensor.

Conversely, when the bush/tree countermeasure level is set undesirably high (a state in which an object is not detected unless the total movement distance of the object is long (for example, approximately 100 cm)), it becomes difficult to perform detection on a human body moving laterally across the detection area (objects whose movement condition involves little change in relative distance from the microwave sensor), and in this case also the reliability of the microwave sensor cannot be maintained.

Accordingly, it is conceivable to automatically vary the bush/tree countermeasure level in a plurality of stages in response to factors such as conditions of the location where the microwave sensor is installed at that time. FIG. 9 is a graph showing an example of a bush/tree countermeasure level setting in a conventional technology microwave sensor. FIG. 10 is an explanatory diagram of adding and subtracting a status counter for the bush/tree countermeasure level setting. Here, a status counter SC is a counter that corresponds to an internal condition of the microwave sensor and its value is limited to a range of 0 to 100.

In the setting examples shown in these drawings, the bush/tree countermeasure levels are switchable between "none", "weak", and "strong". Specifically, in an initial state and when the status counter SC is less than 30, the bush/tree countermeasure level is set to 0 m (none), when the status counter SC is 30 or more but less than 70, the bush/tree countermeasure level is set to 0.4 m (weak), and when the status counter SC is 70 or more, the bush/tree countermeasure level is set to 0.6 m (strong).

Then, in a case where the movement distance of a detected object has exceeded the bush/tree countermeasure level but it has been determined that that is a false alarm since nothing has been detected by a combined PIR sensor for example, a certain value is added to the status counter SC. By doing this, when false alarms continue a plurality of times, the value of the status counter SC increases and eventually the bush/tree countermeasure level is set one stage higher, and therefore it becomes more difficult for false alarms to occur. If, regardless of this, false alarms further continue, the bush/tree countermeasure level is set another stage higher to suppress the occurrences of false alarms. On the other hand, when a state continues in which no object is being detected, the status counter SC value is decreased gradually.

In other words, even when the bush/tree countermeasure level once becomes large as described above, if a state of no false alarms continues, the bush/tree countermeasure level is incrementally reduced and may eventually return to 0 m. By configuring in this manner, the bush/tree countermeasure level can be automatically changed among a plurality of stages and it is possible to achieve reductions in false alarms of the microwave sensor and improvements in reliability.

SUMMARY OF THE INVENTION

However, with this configuration, the status counter SC value is increased when false alarms continue to occur wherein the movement distance of an object that has been detected exceeds the bush/tree countermeasure level. For this reason, if a state continues for a long time in which the movement distance of a detected object is slightly below the bush/tree countermeasure level at that time, there will be no increase in the status counter SC value. Thereafter, when the movement distance of the detected object slightly exceeds the bush/tree countermeasure level, a false alarm will be produced undesirably as a result. Furthermore, there is a problematical point in that an unstable state may arise in which false alarms occur quite easily when the bush/tree countermeasure level is in the "none" state.

An object of the present invention is to provide a microwave sensor in which false alarms are prevented as much as possible and operational reliability is improved by enabling more accurate discrimination between a bush or tree or the like swaying in the wind and a detection target object such as an intruder using a simple configuration.

A microwave sensor according to the present invention is a microwave sensor that transmits a plurality of microwaves of different frequencies toward a detection area and is capable of detecting a distance to a detection target object based on reflected waves of the respective microwaves from the detection target object present in the detection area, provided with: a movement distance measuring means or device that measures as a movement distance of the detection target object an amount of change per unit of time in a distance to the detected detection target object, an alarm signal output control means or device that performs control such that an alarm signal is outputted when the movement distance measured by the movement distance measuring means is a predetermined determination threshold value or more, and a determination threshold value varying means or device that varies the determination threshold value to a larger value when a state in which the movement distance is not less than the determination threshold value continues for not less than a first predetermined period and when a state in which the movement distance is less than the determination threshold value and a difference between the determination threshold value and the movement distance is not greater than a predetermined value continues for not less than a second predetermined period.

Here, the first predetermined period is not greater than the second predetermined period. However, these periods are not necessarily determined as direct units of time. For example, a counter of some kind may be used to determine this in response to a number of times of measurement of the movement distance, but there is no limitation to this. Furthermore, it is preferable that the determination threshold value varying means varies the determination threshold value to a smaller value when a state in which the movement distance is less than the determination threshold value and a difference between the determination threshold value and the movement distance is greater than the predetermined value continues for not less than a third predetermined period (which is determined to be not less than the second predetermined period).

With the thus-configured microwave sensor, even when the movement distance measured by the movement distance measuring means is slightly smaller than the determination threshold value, the determination threshold value is automatically set to a larger value by the continuance of that state over a certain period. That is, by increasing the determination threshold value in advance not only when an actual false alarm has occurred but when a condition is identified in which the probability of an occurrence of a false alarm is increasing, it is possible to prevent in advance occurrences of actual false alarms. This enables false alarms to be avoided as much as possible and increases operational reliability.

Furthermore, in the microwave sensor according to the present invention, the determination threshold value may be established within a predetermined range in which a value greater than zero is set as a lower limit value. For example, the determination threshold value may be set as one of incremental values within the predetermined range.

With the thus-configured microwave sensor, the determination threshold value is always set to a value not less than the lower limit value, and therefore it is possible to eliminate, as much as possible, situations in which an unstable state arises such that false alarms occur regardless of the movement distance being an extremely small value, and there being a low probability that there is an intruder, or the like.

Furthermore, the microwave sensor according to the present invention may be further provided with a passive-type infrared sensor that receives infrared rays from within the detection area and detects an intruding object from a temperature difference from a surrounding area, wherein output of the alarm signal is allowed only when the passive-type infrared sensor is detecting an intruding object.

With the thus-configured microwave sensor, even when, for example, a comparison is made between the movement distance and the determination threshold value, and a determination is made inadvertently that there is a detection target object, such as an intruder, due to a bush or tree, or the like swaying in the wind, there is no output of the alarm signal unless the passive-type infrared sensor is simultaneously detecting the intruding object. This enables false alarms to be prevented from being issued outside the microwave sensor and makes it possible to further increase operational reliability.

With a microwave sensor according to the present invention, by varying in advance the determination threshold value for distinguishing between a bush or tree, or the like, swaying in the wind and a detection target object such, as an intruder, not only when an actual false alarm has occurred, but when a condition is identified in which the probability of an occurrence of a false alarm is increasing, occurrences of actual false alarms can be prevented in advance. This enables false alarms to be avoided, as much as possible, and increases operational reliability.

DETAILED DESCRIPTION OF THE INVENTION

Hereinafter, embodiments of the present invention are described with reference to the accompanying drawings. Here description is given of a case in which a microwave sensor is used as a security sensor and a case where the present invention is applied to a microwave sensor in which two types of microwaves of different frequencies are used to determine a detection target object (an intruder or the like).

First Embodiment

Figure 1:
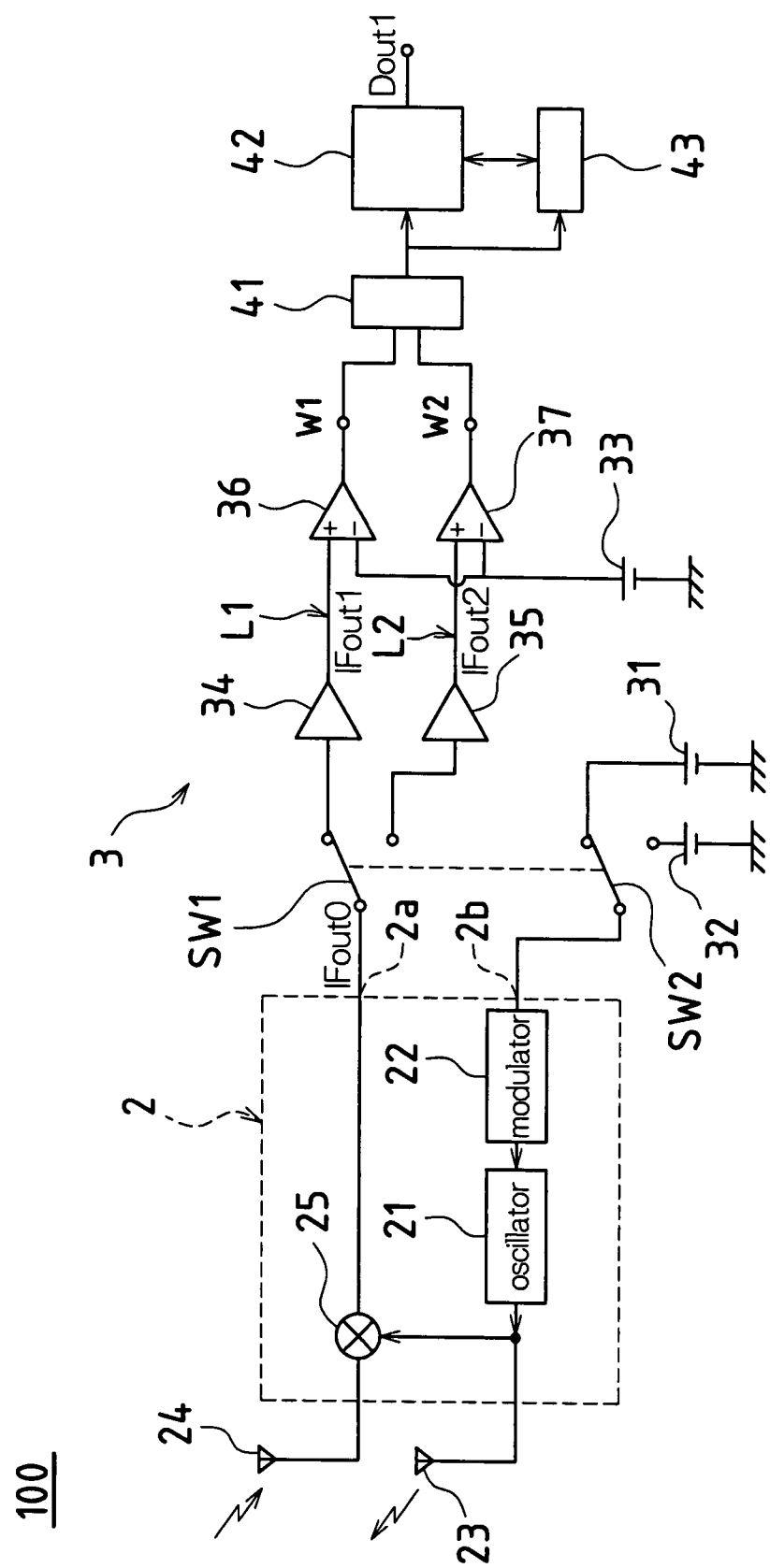
FIG. 1 is a schematic diagram of a circuit configuration of a microwave sensor according to a first embodiment of the present invention.
Figure 2:
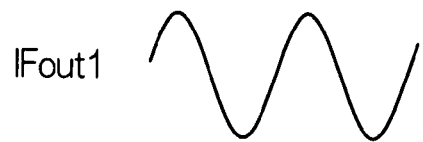
FIG. 2(a) and FIG. 2(b) are waveform diagrams of IF output signals in a dual frequency type microwave sensor, with FIG. 2(a) showing one IFout1 and FIG. 2(b) showing another IFout2.
Figure 2:
Figure 3:
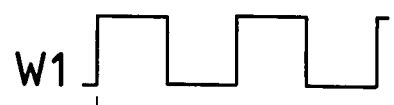
FIG. 3(a) and FIG. 3(b) are waveform diagrams of rectangular waves obtained by performing waveform shaping on the IF output signals of FIG. 2(a) and FIG. 2(b), with FIG. 3(a) showing one rectangular wave W1 and FIG. 3(b) showing the other rectangular wave W2.
Figure 3:
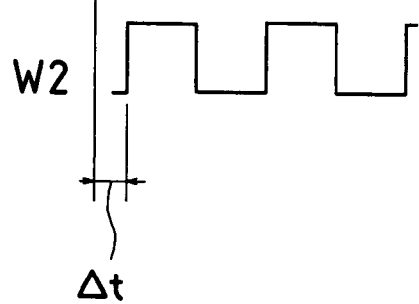

FIG. 1 is a schematic diagram of a circuit configuration of a microwave sensor 100 according to a first embodiment of the present invention. FIG. 2(a) and FIG. 2(b) are waveform diagrams of IF output signals in a dual frequency type microwave sensor such as the microwave sensor 100, with FIG. 2(a) showing one IFout1 and FIG. 2(b) showing another IFout2. FIG. 3(a) and FIG. 3(b) are waveform diagrams of rectangular waves obtained by performing waveform shaping on the IF output signals, with FIG. 3(a) showing one rectangular wave W1 and FIG. 3(b) showing the other rectangular wave W2.

As shown in FIG. 1, the microwave sensor 100 is provided with an RF module 2 that carries out tasks such as transmitting and receiving microwaves and a signal processing portion 3 that carries out tasks, such as processing the output from the RF module 2.

The RF module 2 is provided with an oscillator 21 that oscillates microwaves, a modulator 22 for switching frequencies of the microwaves oscillated from the oscillator 21, a transmitting antenna 23 that transmits the microwaves oscillated from the oscillator 21 toward a detection area, a receiving antenna 24 that receives reflected waves of microwaves reflected by an object such as a human body, and a mixer 25 that mixes for output the received microwaves and voltage waveforms of the oscillator 21. That is, when an object is present in the detection area, the microwaves transmitted toward the detection area from the transmitting antenna 23 are received at the receiving antenna 24 with the frequencies of the reflected waves from the object modulated due to the Doppler Effect. After the received reflected waves undergo mixing with voltage waveforms of the oscillator 21 by the mixer 25, they are outputted to the analog signal processing portion 3 as an IF output signal (IFout0) from an output side 2a of the RF module 2.

The signal processing portion 3 is provided with a first output line L1 having an IF amplifier 34 and a comparator 36, and a second output line L2 having an IF amplifier 35 and a comparator 37, which correspond respectively to each microwave of each frequency transmitted from the transmitting antenna 23, and a power source 33 that is a reference voltage for the comparators 36 and 37. Further still, power sources 31 and 32 are provided to enable the RF module 2 to oscillate the two types of microwaves, and a movement distance measuring portion 41, an alarm signal output portion 42, and a bush/tree countermeasure level varying portion 43 are provided on an output side of the comparators 36 and 37.

The IF amplifiers 34 and 35 are connected to the output side 2a of the RF module 2 via a first switch SW1. The first switch SW1 is switchable such that, when one of the aforementioned two types of microwaves is being transmitted from the transmitting antenna 23, it connects to the first output line L1, and when the other microwave is being transmitted from the transmitting antenna 23, it connects to the second output line L2. In other words, this device is configured so that when one of the microwaves is being transmitted, the IF output signal pertaining to reflected waves reflected by an object are outputted to the first output line L1, and when the other of the microwaves is being sent, the IF output signal pertaining to reflected waves reflected by the object are outputted to the second output line L2.

Furthermore, the power sources 31 and 32 are connected to an input side 2b of the RF module 2 via a second switch SW2 that is linked to the first switch SW1. This second switch SW2 is also configured so that its connection state with respect to the power sources 31 and 32 switches depending on which microwave of the two types of microwaves is being transmitted from the transmitting antenna 23. In other words, this is configured so that the modulator 22 switches the microwave frequency between a state in which the second switch SW2 is connected to the power source 31 on the one hand and a state in which it is connected to the power source 32 on the other hand, and this enables the frequency of the microwaves transmitted from the transmitting antenna 23 to be switched.

In this manner, accompanying a switching operation of the first switch SW1 and the second switch SW2, two processing operations (a first processing operation and a second processing operation) are configured to be switchable having a predetermined time interval (for example, an interval of several milliseconds). Here, "first processing operation" refers to an operation in which microwaves of one of the frequencies are transmitted from the transmitting antenna 23 toward the detection area, then, an IF output signal based on reflected waves thereof is outputted to the first output line L1 of the signal processing portion 3 and signal processing is carried out in the first output line L1. And "second processing operation" refers to an operation in which microwaves of the other of the frequencies are transmitted from the transmitting antenna 23 toward the detection area, then, an IF output signal based on reflected waves thereof is outputted to the second output line L2 of the signal processing portion 3 and signal processing is carried out in the second output line L2. And in the first processing operation, the IF output signal outputted from the RF module 2 is amplified by the IF amplifier 34, and after the output (IFout1) from the IF amplifier 34 is formed into a rectangular wave W1 by the comparator 36, the rectangular wave W1 is outputted to the movement distance measuring portion 41. The second processing operation is similarly configured such that the IF output signal outputted from the RF module 2 is amplified by the IF amplifier 35, and after the output (IFout2) from the IF amplifier 35 is formed into a rectangular wave W2 by the comparator 37, rectangular wave W2 is outputted to the movement distance measuring portion 41.

When no object, such as a human body, or the like, is present in the detection area, the microwave frequency transmitted from the transmitting antenna 23 and the microwave frequency received at the receiving antenna 24 are equivalent, and therefore the IF frequency in the output signals from the IF amplifiers 34 and 35 are "0", and no signal is outputted from the comparators 36 and 37. In contrast to this, when a human body, or the like, is present in the detection area, the microwave frequency received at the receiving antenna 24 has undergone modulation and is different from the microwave frequency transmitted from the transmitting antenna 23, and therefore a change is produced in the output signal waveform of the comparators 36 and 37 such that the resultant rectangular waves are outputted to the movement distance measuring portion 41.

The movement distance measuring portion 41 receives the output signal waveforms from the comparators 36 and 37 and determines a relative distance to the object present in the detection area based on these output signal waveforms. As mentioned earlier, the phase difference between the two IF output signals (IFout1 and IFout2) correlates to the relative distance to the object such that there is a tendency for greater phase differences to occur for greater relative distances to the object, and therefore the relative distance to the object can be obtained from the phase difference. Further still, a movement distance $\Delta d$ of the object per unit of time (not a speed, but a distance by which the object has actually moved in one second for example) is measured by performing this continuously and identifying change over time.

The alarm signal output portion 42 performs a magnitude comparison on the movement distance $\Delta d$ of the object per unit of time, which is outputted from the movement distance measuring portion 41, and a determination threshold value (bush/tree countermeasure level X) for determining whether or not a detected object is a bush or tree or the like swaying in the wind. If the movement distance $\Delta d$ is smaller than the bush/tree countermeasure level X, then there is a high probability that the detected object is a bush or tree or the like, and therefore an OFF state is maintained for the output of the alarm signal Dout1. On the other hand, if the movement distance $\Delta d$ is not less than the bush/tree countermeasure level X, then there is a high probability that the detected object is an intruder or the like, and therefore the output of the alarm signal Dout1 is set to ON.

Figures 4, 5:
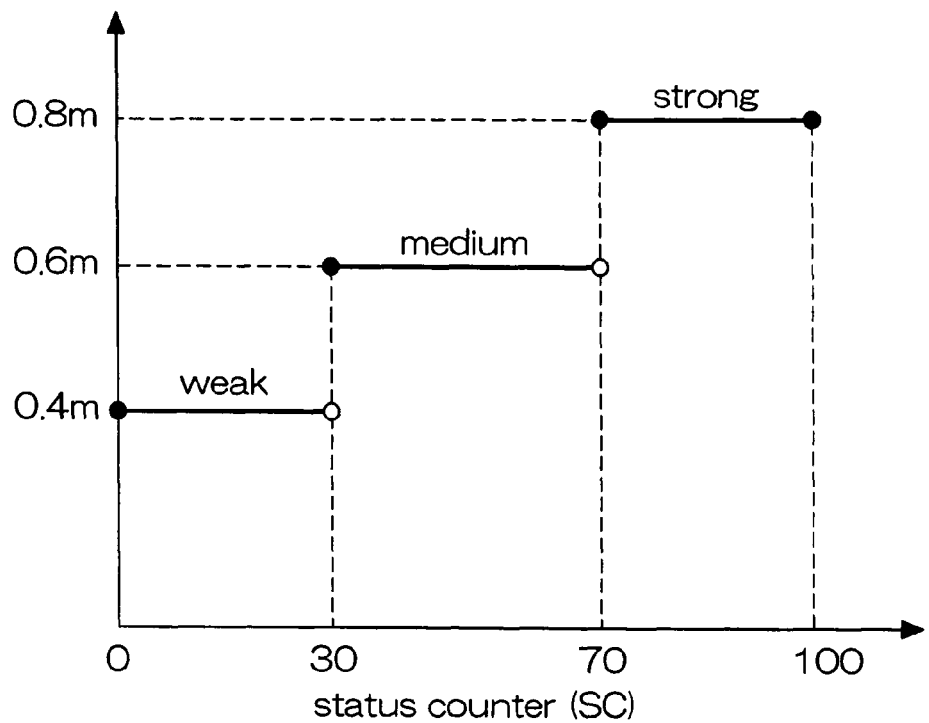
FIG. 4 is a graph showing an example of a bush/tree countermeasure level setting in a microwave sensor according to a first embodiment of the present invention.
FIG. 5 is an explanatory diagram of adding and subtracting a status counter for the bush/tree countermeasure level setting in a microwave sensor according to the first embodiment of the present invention.

The bush/tree countermeasure level varying portion 43 has a function of automatically varying in a plurality of stages within a predetermined range the bush/tree countermeasure level X that is referenced at the alarm signal output portion 42. FIG. 4 is a graph showing example settings of the bush/tree countermeasure level X. FIG. 5 is an explanatory diagram of adding and subtracting the status counter SC for the bush/tree countermeasure level X setting. Here, the status counter SC is a counter that corresponds to an internal condition of the microwave sensor 100 and its value is limited to a range of 0 to 100.

As shown in FIG. 4, the bush/tree countermeasure level X is switchable between three stages of "weak", "medium", and "strong". Specifically, in an initial state and when the status counter SC is less than 30, the bush/tree countermeasure level X is set to 0.4 m (weak), when the status counter SC is 30 or more but less than 70, the bush/tree countermeasure level X is set to 0.6 m (medium), and when the status counter SC is 70 or more, the bush/tree countermeasure level X is set to 0.8 m (strong).

Then, based on the magnitude relationship and the difference thereof between the movement distance $\Delta d$ of the detected object and the bush/tree countermeasure level X, addition/subtraction calculations are performed on the status counter SC as shown in FIG. 5. That is, in a case where the movement distance $\Delta d$ of the detected object has exceeded the bush/tree countermeasure level X but it has been determined that that is a false alarm since nothing has been detected by a combined PIR sensor for example, an addition of one of 20, 30, or 40 is made to the status counter SC according to the difference between the movement distance $\Delta d$ and the bush/tree countermeasure level X. And when the difference between these is small even though the movement distance $\Delta d$ has not exceeded the bush/tree countermeasure level X, an addition of 10 is made to the status counter SC.

It should be noted that the addition value when the movement distance $\Delta d$ is not exceeding the bush/tree countermeasure level X is smaller than the addition value when the movement distance $\Delta d$ is exceeding the bush/tree countermeasure level X, and therefore the number of times of additions required until the bush/tree countermeasure level X increases by one stage is smaller when the movement distance $\Delta d$ is exceeding the bush/tree countermeasure level X.

On the other hand, when a state continues in which no object is being detected, the status counter SC value is decreased by increments of 1.

For example, when the status counter SC is 0 at the initial state, the bush/tree countermeasure level X is set to 0.4 m (weak), but when the movement distance $\Delta d$ measured at that time is 0.5 m, an addition of 20 is made to the status counter SC. If the same continues to happen one more time, then a further addition of 20 is made to the status counter SC and it becomes 40 so that the bush/tree countermeasure level X is set one stage up to 0.6 m (medium). When the next measured movement distance $\Delta d$ is 0.7 m, a further addition of 20 is made to the status counter SC and it becomes 60, and if the same continues to happen one more time, then a further addition of 20 is made to the status counter SC and it becomes 80 so that the bush/tree countermeasure level X is set another stage up to 0.8 m (strong). That is, in this case, the number of times of measurements of the movement distance Δd required until the bush/tree countermeasure level X reaches from a state of "weak" to "strong" is a total of four times.

When the movement distance Δd measured when the status counter SC is 0 at the initial state is 0.3 m, an addition of 10 is made to the status counter SC. If the same continues to happen a further two times (a total of three times), then the status counter SC becomes 30 so that the bush/tree countermeasure level X is set one stage up to 0.6 m (medium). When the next measured movement distance Δd is 0.5 m, an addition of 10 is made to the status counter SC. If the same continues to happen a further three times (a total of four times), then the status counter SC becomes 70 so that the bush/tree countermeasure level X is set another stage up to 0.8 m (strong). That is, in this case, the number of times of measurements of the movement distance Δd required until the bush/tree countermeasure level X reaches from a state of "weak" to "strong" is a total of seven times.

Furthermore, if the movement distance Δd is not detected after the status counter SC has reached 80 and the bush/tree countermeasure level X has been set to "strong", then the status counter SC becomes 69 after measurements of the movement distance Δd have been carried out a further 11 times, and the bush/tree countermeasure level X is set to "medium", and the status counter SC becomes 29 after measurements of the movement distance Δd have been carried out a further 40 times, and the bush/tree countermeasure level X is set to "weak". With the above-described configuration of the first embodiment, additions are made to the status counter SC value even when the movement distance Δd of the detected object is slightly smaller than the bush/tree countermeasure level X. And when this state continues over a certain period, the bush/tree countermeasure level X is automatically set larger. That is, by increasing the bush/tree countermeasure level X in advance not only when an actual false alarm has occurred but when a condition is identified in which the probability of an occurrence of a false alarm is increasing, it becomes possible to prevent in advance as much as possible occurrences of actual false alarms. Furthermore, by setting the smallest value of the bush/tree countermeasure level X not to zero but setting the smallest value to 0.4 m, it is possible to prevent even a temporary lapse into an unstable state in which false alarms occur easily.

Second Embodiment

Hereinafter description is given of a configuration as second embodiment in which a portion of the signal processing portion 3 of the microwave sensor 100 of the first embodiment is replaced by software processing on a one-chip microcomputer for device integration. It should be noted that points other than those discussed below are the same as in the first embodiment, and therefore the same reference numerals are applied to the same structural members and description is given mainly concerning the points of difference.

Figure 6:
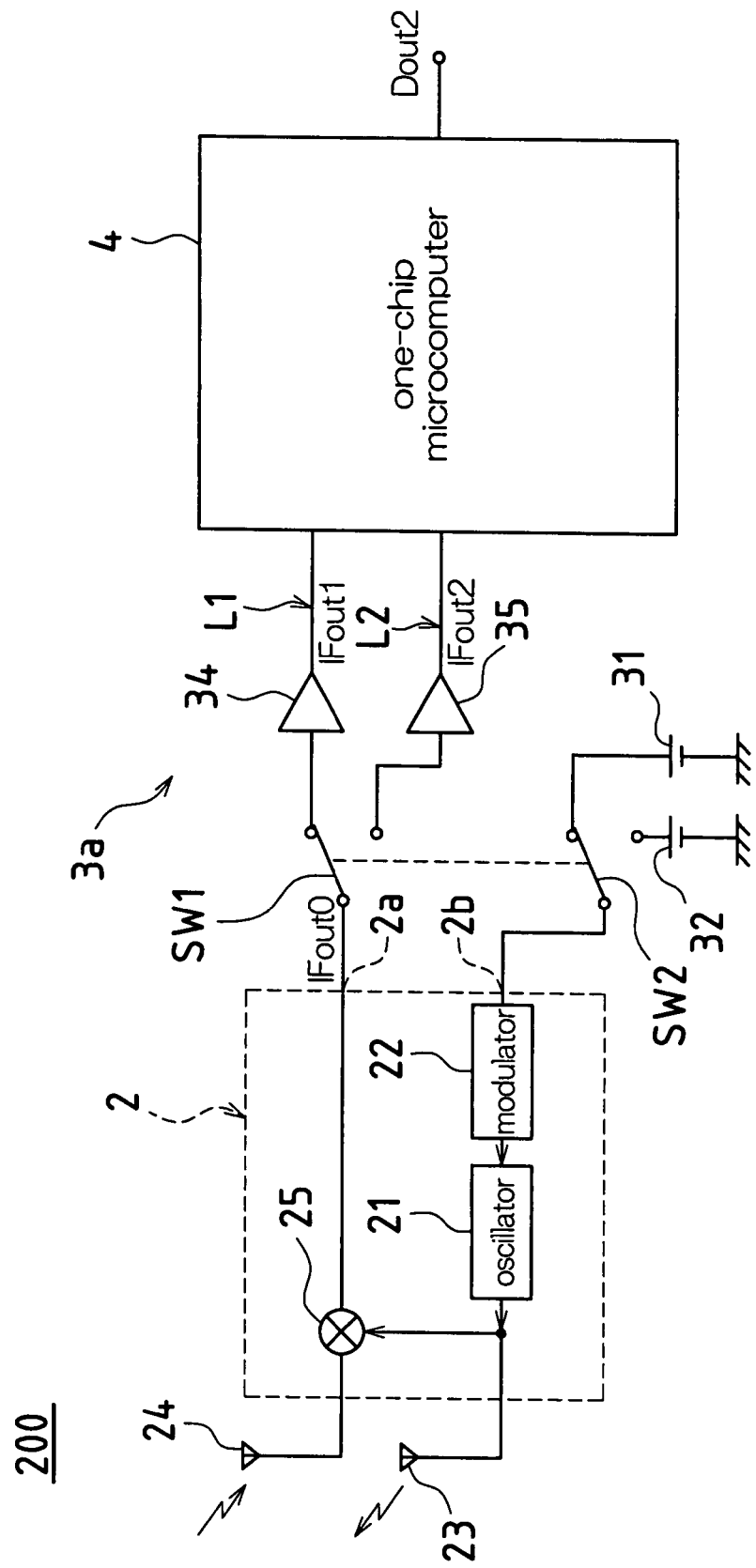
FIG. 6 is a schematic drawing of a circuit configuration of a microwave sensor according to a second embodiment of the present invention.

FIG. 6 is a schematic drawing of a circuit configuration of a microwave sensor 200 according to the second embodiment of the present invention. As shown in the diagram, the RF module 2 is the same as in the first embodiment, and the signal processing portion 3a is in common with the first embodiment up to the IF amplifier 34 and IF amplifier 35. In the second embodiment, functioning equivalent to the various signal processes and computations of the comparator 36, the comparator 37, the power source 33, the movement distance measuring portion 41, the alarm signal output portion 42, and the bush/tree countermeasure level varying portion 43 of the first embodiment are all achieved by a control program stored on a one-chip microcomputer 4.

The one-chip microcomputer 4 has ports such as an input port, an A/D input port, and an output port. The output (IFout1) from the IF amplifier 34 and the output (IFout2) from the IF amplifier 35 are respectively connected to the A/D input port. An alarm signal Dout2 outputted from the output port is ON when a detection target object has been detected.

Figure 7:
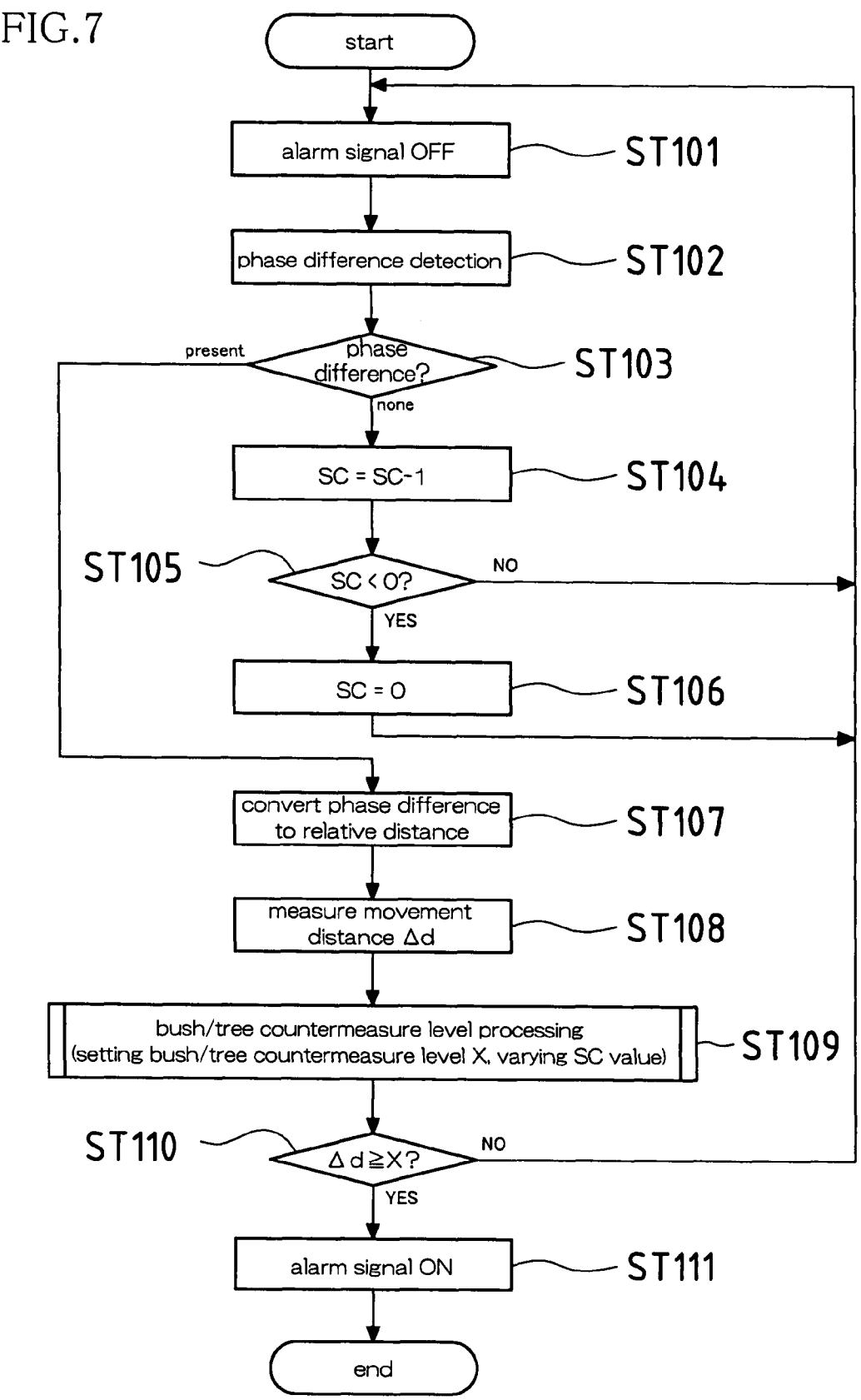
FIG. 7 is a schematic process flowchart of the control program carried out in the one-chip microcomputer of the microwave sensor according to the second embodiment of the present invention.

FIG. 7 is a schematic process flowchart of the control program carried out in the one-chip microcomputer 4 of the microwave sensor 200 according to the second embodiment of the present invention.

As shown in FIG. 7, at the beginning of processing, the alarm signal Dout2 is initialized at OFF (step ST101). Next, phase difference between the IFout1 and the IFout2 is detected (step ST102). Then a determination is carried out (step ST103) as to whether or not there is a phase difference, and if a phase difference is detected, then the procedure proceeds to step ST107, otherwise the procedure proceeds to the next step, step ST104.

If no phase difference is detected, the value of the status counter SC for setting the bush/tree countermeasure level is reduced by 1 (step ST104). Here, the value of the status counter SC is limited to a range of 0 to 100, and a magnitude comparison is carried out (step ST105) with "0", which is the lower limit value thereof, and when this is less than "0", it is set (step ST106) to "0", the lower limit value for the status counter SC, and either way the procedure returns to step ST101.

When phase difference has been detected, calculations are carried out (step ST107) for converting the detected phase difference to a relative distance from the microwave sensor 200. Further still, to implement the "bush/tree countermeasures", the movement distance Δd of the object (the amount of change per unit of time in the relative distance) is detected (step ST108) based on change over time in the relative distance.

Next, "bush/tree countermeasure level processing" subroutine is called, and the bush/tree countermeasure level X, which is the determination threshold value of the movement distance Δd, is set to an appropriate value based on the value of the status counter SC at that point in time, then the value of the status counter SC is varied (step ST109) based on the status counter SC value at that point in time as well as a difference between the movement distance Δd and the bush/tree countermeasure level X. It should be noted that specific processing in the "bush/tree countermeasure level processing" subroutine is described later with reference to FIG. 8.

Then, a magnitude comparison is carried out (step ST110) on the movement distance Δd and the bush/tree countermeasure level X, and when the movement distance Δd is not less than the bush/tree countermeasure level X, the procedure proceeds to the next step, step ST111, and processing finishes after the alarm signal Dout2 is set to ON. When the movement distance Δd is less than the bush/tree countermeasure level X, then the probability of an effect of a bush or tree or the like is high and therefore the procedure returns to step ST101.

Figure 8:
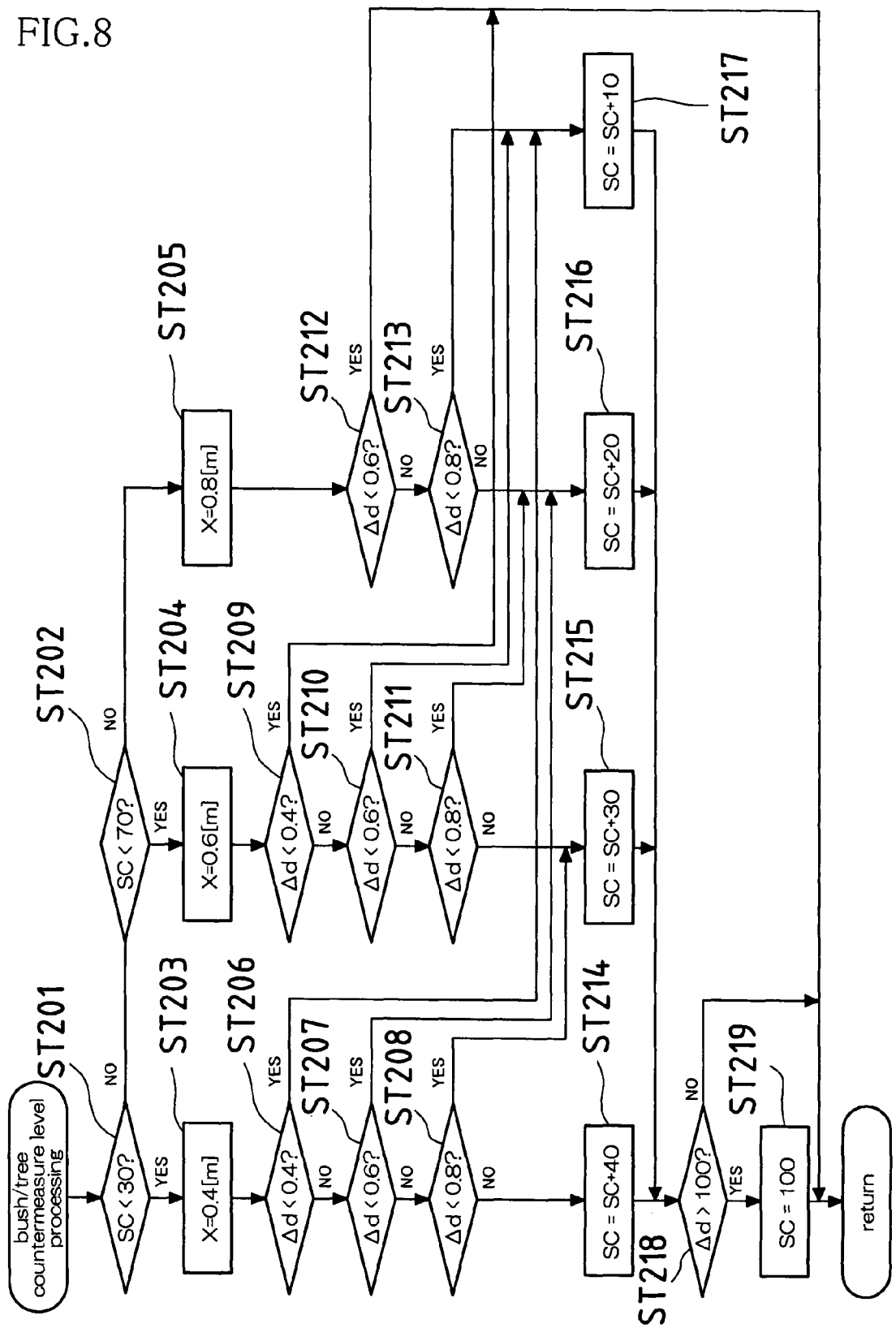
FIG. 8 is a schematic process flowchart of the "bush/tree countermeasure level processing" subroutine carried out in the flowchart of FIG. 7.
Figures 9, 10:
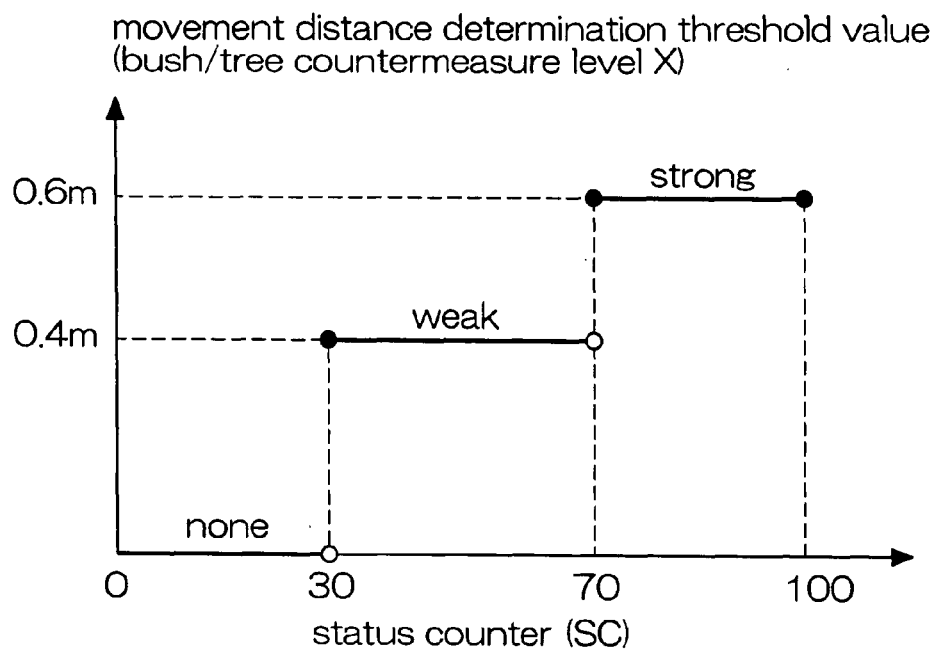
FIG. 9 is a graph showing an example of a bush/tree countermeasure level setting in a conventional technology microwave sensor.
FIG. 10 is an explanatory diagram of adding and subtracting a status counter for the bush/tree countermeasure level setting in a conventional technology microwave sensor.

FIG. 8 is a schematic process flowchart of the "bush/tree countermeasure level processing" subroutine carried out in the flowchart of FIG. 7.

As shown in FIG. 8, when the status counter SC is less than 30, the bush/tree countermeasure level X is set to 0.4 m, when the status counter SC is 30 or more but less than 70, the bush/tree countermeasure level X is set to 0.6 m, and when the status counter SC is 70 or more, the bush/tree countermeasure level X is set to 0.8 m.

Consequently, first the value of the status counter SC undergoes a sorting process (step ST201 and ST202) and when the status counter SC is less than 30, the bush/tree countermeasure level X is set to 0.4 m (step ST203), when the status counter SC is 30 or more but less than 70, the bush/tree countermeasure level X is set to 0.6 m (step ST204), and when the status counter SC is 70 or more, the bush/tree countermeasure level X is set to 0.8 m (step ST205).

Furthermore, when the status counter SC is less than 30, the following further processing is carried out and the status counter SC value is varied based on the difference between the movement distance Δd and the bush/tree countermeasure level X. That is, the value of the movement distance Δd undergoes a sorting process (steps ST206 to ST208) and when the movement distance Δd is less than 0.4 m, an addition of 10 is made (step ST217) to the value of the status counter SC, when the movement distance Δd is not less than 0.4 m but less than 0.6 m, an addition of 20 is made (step ST216) to the value of the status counter SC, when the movement distance Δd is not less than 0.6 m but less than 0.8 m, an addition of 30 is made (step ST215) to the value of the status counter SC, and when the movement distance Δd is 0.8 m or more, an addition of 40 is made (step ST214) to the value of the status counter SC. For any of these the procedure then proceeds to step ST218.

When the status counter SC is 30 or more but less than 70, the following further processing is carried out and the status counter SC value is varied based on the difference between the movement distance Δd and the bush/tree countermeasure level X. That is, the value of the movement distance Δd undergoes a sorting process (steps ST209 to ST211) and when the movement distance Δd is not less than 0.4 m but less than 0.6 m, an addition of 10 is made (step ST217) to the value of the status counter SC, when the movement distance Δd is not less than 0.6 m but less than 0.8 m, an addition of 20 is made (step ST216) to the value of the status counter SC, and when the movement distance Δd is 0.8 m or more, an addition of 30 is made (step ST215) to the value of the status counter SC, and for any of these times the procedure then proceeds to step ST218. It should be noted that when the movement distance Δd is less than 0.4 m, the value of the status counter SC remains as it is and the procedure returns to the flow chart in FIG. 7.

When the status counter SC is 70 or more, the following further processing is carried out and the status counter SC value is varied based on the difference between the movement distance Δd and the bush/tree countermeasure level X. That is, the value of the movement distance Δd undergoes a sorting process (steps ST212 and ST213) and when the movement distance Δd is not less than 0.6 m but less than 0.8 m, an addition of 10 is made (step ST217) to the value of the status counter SC, and when the movement distance Δd is 0.8 m or more, an addition of 20 is made (step ST216) to the value of the status counter SC, and for either of these times the procedure then proceeds to step ST218. It should be noted that when the movement distance Δd is less than 0.6 m, the value of the status counter SC remains as it is and the procedure returns to the flow chart in FIG. 7.

Furthermore, the upper limit value of the status counter SC is "100", and therefore when a magnitude comparison is carried out (step ST218) between the status counter SC value after it has been varied and the upper limit value "100" and it is greater than "100", it is set to "100" (step ST219), which is the upper limit value of the status counter SC. And for either of these the procedure returns to the flowchart of FIG. 7 from where this subroutine was called.

Other Embodiments

Figure 11:
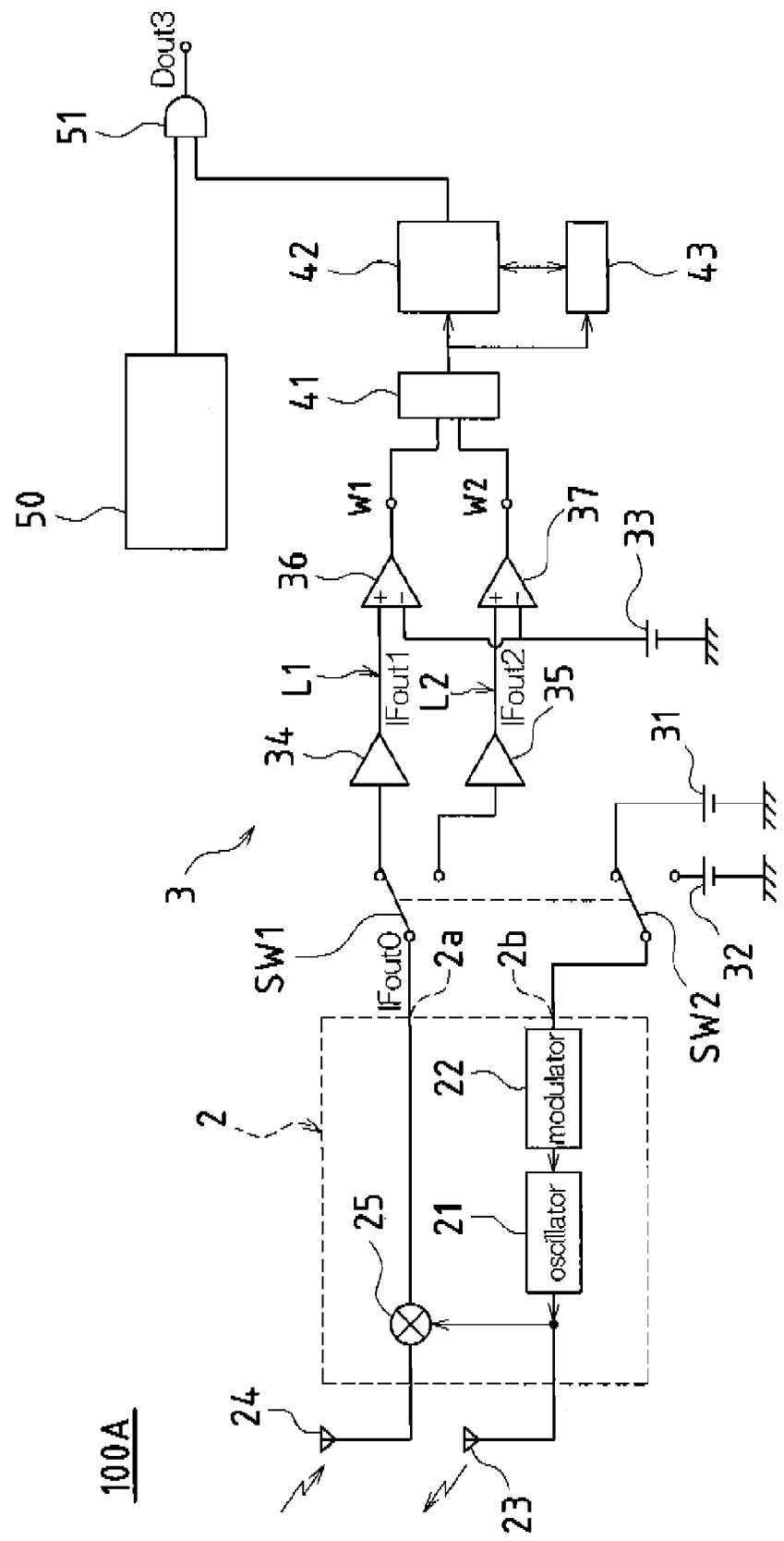
FIG. 11 is a schematic diagram of a circuit configuration of a microwave sensor according to another embodiment of the present invention.

Application of the present invention is not limited to a microwave sensor configured to determine detection target objects using two types of microwaves of different frequencies and may be applied to a microwave sensor configured to determine detection target objects using three types or more of microwaves of different frequencies. Furthermore, this may be a so-called combination sensor in which AND detection is carried out by a combination with a passive-type infrared sensor. In FIG. 11 such a combination sensor is shown as a microwave sensor 100A, further including a passive-type infrared sensor 50 and an AND gate 51 in addition to all components shown in FIG. 1. The output from the passive-type infrared sensor 50 and the output from the alarm signal output portion 42 are respectively connected to the input port of the AND gate 51, which outputs an alarm signal Dout3.

Furthermore, some of the circuits or the like in the above-described microwave sensor can also be easily achieved by a programmable logic device (PLD) or a field programmable gate array (FPGA) or the like for example.

The present invention can be embodied and practiced in other different forms without departing from the spirit and essential characteristics thereof. Therefore, the above-described embodiments are considered in all respects as illustrative and not restrictive. The scope of the invention is indicated by the appended claims rather than by the foregoing description. All variations and modifications falling within the equivalency range of the appended claims are intended to be embraced therein.

It should be noted that this application claims priority on Patent Application No. 2005-128428 filed in Japan on Apr. 26, 2005, the entire contents of which are hereby incorporated by reference. Furthermore, documents cited in this specification are hereby specifically incorporated in their entirety by reference.

The present invention may be suitably applied to security sensors or the like that detect an intruder or the like intruding into a detection area and issue an alarm.

The invention claimed is:

1. A microwave sensor that transmits a plurality of microwaves of different frequencies toward a detection area and is capable of detecting a distance to a detection target object based on reflected waves of the microwaves from the detection target object present in the detection area, said microwave sensor comprising:
   a movement distance measuring device configured to measure, as a movement distance of the detection target object, an amount of change per unit of time in a distance to the detected detection target object;
   an alarm signal output control device configured to perform control such that an alarm signal is outputted when the movement distance measured by said movement distance measuring device is a predetermined determination threshold value or more; and
   a determination threshold value varying device configured to vary the determination threshold value to a larger value when a state in which the movement distance is not less than the determination threshold value continues for not less than a first predetermined period and when a state in which the movement distance is less than the determination threshold value and a difference between the determination threshold value and the movement distance is not greater than a predetermined value continues for not less than a second predetermined period.

2. The microwave sensor according to claim 1, wherein the determination threshold value varying device is configured to vary the determination threshold value to a smaller value when a state in which the movement distance is less than the determination threshold value and a difference between the determination threshold value and the movement distance is greater than the predetermined value continues for not less than a third predetermined period.

3. The microwave sensor according to claim 2, wherein the first predetermined period is not greater than the second predetermined period, and the second predetermined period is not greater than the third predetermined period.

4. The microwave sensor according to claim 3, wherein the determination threshold value is established within a predetermined range in which a value greater than zero is set as a lower limit value.

5. The microwave sensor according to claim 4, wherein the determination threshold value is set as one of incremental values within the predetermined range.

6. The microwave sensor according to claim 1, further comprising a passive infrared sensor that receives infrared rays from within the detection area and detects an intruding object from a temperature difference from a surrounding area,
wherein output of the alarm signal is allowed only when said passive infrared sensor is detecting an intruding object.

7. The microwave sensor according to claim 2, further comprising a passive infrared sensor that receives infrared rays from within the detection area and detects an intruding object from a temperature difference from a surrounding area,
wherein output of the alarm signal is allowed only when the said passive infrared sensor is detecting an intruding object.

8. The microwave sensor according to claim 3, further comprising a passive infrared sensor that receives infrared rays from within the detection area and detects an intruding object from a temperature difference from a surrounding area,
wherein output of the alarm signal is allowed only when the said passive infrared sensor is detecting an intruding object.

9. The microwave sensor according to claim 4, further comprising a passive infrared sensor that receives infrared rays from within the detection area and detects an intruding object from a temperature difference from a surrounding area,
wherein output of the alarm signal is allowed only when the said passive infrared sensor is detecting an intruding object.

10. The microwave sensor according to claim 5, further comprising a passive infrared sensor that receives infrared rays from within the detection area and detects an intruding object from a temperature difference from a surrounding area,
wherein output of the alarm signal is allowed only when the said passive infrared sensor is detecting an intruding object.

* * * * *